United States Patent
Doerr et al.

(10) Patent No.: US 12,337,186 B2
(45) Date of Patent: Jun. 24, 2025

(54) IMPLANTABLE PULSE GENERATOR HAVING RECTANGULAR SHOCK WAVEFORM

(71) Applicant: BIOTRONIK SE & Co. KG, Berlin (DE)

(72) Inventors: Thomas Doerr, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 327 days.

(21) Appl. No.: 17/630,323

(22) PCT Filed: Jul. 21, 2020

(86) PCT No.: PCT/EP2020/070535
§ 371 (c)(1),
(2) Date: Jan. 26, 2022

(87) PCT Pub. No.: WO2021/023506
PCT Pub. Date: Feb. 11, 2021

(65) Prior Publication Data
US 2022/0249853 A1    Aug. 11, 2022

(30) Foreign Application Priority Data

Aug. 6, 2019  (EP) ..................... 19190314

(51) Int. Cl.
*A61N 1/39*   (2006.01)
*H02J 7/00*   (2006.01)
(Continued)

(52) U.S. Cl.
CPC ......... *A61N 1/3912* (2013.01); *A61N 1/3956* (2013.01); *A61N 1/3975* (2013.01);
(Continued)

(58) Field of Classification Search
CPC ... A61N 1/3912; A61N 1/3956; A61N 1/3975
See application file for complete search history.

(56) References Cited

U.S. PATENT DOCUMENTS

| | | | | |
|---|---|---|---|---|
| 5,366,484 A | * | 11/1994 | Kroll | ............ A61N 1/3956 607/5 |
| 5,391,186 A | * | 2/1995 | Kroll | ............ A61N 1/3956 607/5 |

(Continued)

FOREIGN PATENT DOCUMENTS

| | | |
|---|---|---|
| EP | 0135735 A1 | 4/1985 |
| EP | 1163929 A2 | 12/2001 |

OTHER PUBLICATIONS

International Search Report (PCT/ISA/210) and Written Opinion (PCT/ISA/237) mailed on Aug. 6, 2020, by the European Patent Office as the International Searching Authority for International Application No. PCT/EP2020/070535.

*Primary Examiner* — Eric D. Bertram
(74) *Attorney, Agent, or Firm* — Buchanan Ingersoll & Rooney PC

(57) ABSTRACT

The present invention relates an implantable pulse generator comprising an electric circuit, wherein the electric circuit comprises: a primary energy store, at least one secondary energy store, and a control unit, wherein the control unit is configured to activate an electric switch in the electric circuit in such a way that, in a first interval of a first phase of a pulse delivery, the primary energy store is discharged via a therapeutic current path, and to activate an electric switch in the electric circuit in such a way that, in a second interval of the first phase of the pulse delivery, the secondary energy store is discharged via the therapeutic current path, wherein the primary energy store and the at least one secondary energy store are fixedly connected, or connectable, in series, and wherein the implantable pulse generator is designed to
(Continued)

deliver a shock having an approximately rectangular pulse waveform.

14 Claims, 7 Drawing Sheets

(51) Int. Cl.
    *H03K 3/015* (2006.01)
    *H03K 3/57* (2006.01)
(52) U.S. Cl.
    CPC ............ *H02J 7/0025* (2020.01); *H03K 3/015* (2013.01); *H03K 3/57* (2013.01)

(56) References Cited

U.S. PATENT DOCUMENTS

| | | | | |
|---|---|---|---|---|
| 5,395,395 | A | | 3/1995 | Hedberg |
| 5,507,781 | A | * | 4/1996 | Kroll ................... A61N 1/3956 607/7 |
| 5,514,160 | A | * | 5/1996 | Kroll ................... A61N 1/3925 607/5 |
| 5,733,309 | A | * | 3/1998 | Kroll ................... A61N 1/3956 607/5 |
| 6,778,860 | B2 | * | 8/2004 | Ostroff ................ A61N 1/3906 607/70 |
| 7,962,212 | B2 | * | 6/2011 | Signoff ................ H02J 7/0024 607/34 |
| 8,473,051 | B1 | * | 6/2013 | Wessels ................ A61N 1/395 607/7 |
| 2001/0031991 | A1 | * | 10/2001 | Russial ................ A61N 1/3912 607/5 |
| 2002/0049473 | A1 | | 4/2002 | Irnich |
| 2003/0088277 | A1 | * | 5/2003 | Ostroff ................ A61N 1/3906 607/5 |
| 2003/0088281 | A1 | * | 5/2003 | Ostroff ................ A61N 1/3956 607/5 |
| 2003/0216786 | A1 | * | 11/2003 | Russial ................ A61N 1/3912 607/5 |
| 2005/0021094 | A1 | * | 1/2005 | Ostroff ................ A61N 1/3906 607/5 |
| 2005/0177193 | A1 | * | 8/2005 | Nielsen ................ A61N 1/378 607/5 |
| 2015/0306406 | A1 | | 10/2015 | Crutchfield et al. |

* cited by examiner

ID PULSE GENERATOR
HAVING RECTANGULAR SHOCK
WAVEFORM

IMPLANTABLE PULSE GENERATOR HAVING RECTANGULAR SHOCK WAVEFORM

CROSS-REFERENCE TO RELATED APPLICATIONS

This application is the United States National Phase under 35 U.S.C. § 371 of PCT International Patent Application No. PCT/EP2020/070535, filed on Jul. 21, 2020, which claims the benefit of European Patent Application No. 19190314.5, filed on Aug. 6, 2019, the disclosures of which are hereby incorporated by reference herein in their entireties.

TECHNICAL FIELD

The present invention relates to an implantable pulse generator.

BACKGROUND

Presently, capacitor discharges are always used in implantable defibrillators (ICDs) for defibrillation, wherein the entire shock energy is taken from a constant capacitance over the course of the defibrillation. The exponentially dropping voltage waveform is characteristic of this.

Shock waveforms that support a minimized shock voltage are already being used in external defibrillators.

The disadvantage of the exponential shock waveform is the high peak voltages that are needed to carry out effective defibrillation. In particular in the case of non-transvenous defibrillators (for example, subcutaneous ICDS such as S-ICD™), this results in peak voltages in excess of 1300 V, which, in turn, require appropriate high voltage components and compliance with aligned design rules.

The present disclosure is directed toward overcoming one or more of the above-mentioned problems, though not necessarily limited to embodiments that do.

SUMMARY

Based at least thereon, it is an object of the present invention to provide an implantable pulse generator, which can provide a therapeutically effective shock using a lower shock voltage.

At least this object is achieved by an implantable pulse generator having the features of claim 1 and by a method having the features of claim 10. Suitable embodiments are provided in the dependent claims and in the following description.

According to claim 1, an implantable pulse generator comprising an electric circuit is provided. The electric circuit comprises:
a primary energy store;
at least one secondary energy store; and
a control unit, wherein the control unit is configured:
  to activate an electric switch in the electric circuit in such a way that, in a first interval of a first phase of a pulse delivery, the primary energy store is discharged via a therapeutic current path, and
  to activate an electric switch in the electric circuit in such a way that, in a second interval of the first phase of a pulse delivery, the at least one secondary energy store is discharged via the therapeutic current path,
wherein the primary energy store and the at least one secondary energy store are fixedly connected, or connectable, in series, and
wherein the implantable pulse generator is designed to deliver a shock having an approximately rectangular pulse waveform,
wherein the implantable pulse generator comprises multiple secondary energy stores, and
the control unit is further configured to activate an electric switch in the electric circuit in such a way that, in the second interval, the primary energy store and, consecutively, all secondary energy stores are discharged via the therapeutic current path, or
the primary energy store and in each case one of the multiple secondary energy stores are discharged via the therapeutic current path.

In particular, the therapeutic current path is used to deliver a therapeutic electrical pulse to a target tissue, preferably the cardiac tissue of the patient, preferably for the delivery of a therapeutic electric shock for the defibrillation of the cardiac tissue.

Furthermore, in particular the primary energy store and the at least one secondary energy store are discharged, in the second interval of the first phase of the pulse delivery, via the therapeutic current path.

Advantageously, a shock delivery having an approximately rectangular pulse waveform can be achieved by the pulse generator according to the present invention, and in particular a substantially rectangular voltage or current waveform during the pulse delivery. In this way, it is possible to deliver a therapeutically effective (defibrillating) pulse over a defined time, while reducing the maximum required shock voltage. The approach according to the present invention advantageously allows a more cost-effective design for implantable defibrillators, and the use of existing high voltage components and platforms, in particular by reducing the maximum required shock voltage.

The implantable pulse generator according to the present invention is therefore suitable, in particular, for use as a cardioverter defibrillator, so that it is possible to achieve therapy voltages of up to 1200 V having the above-described rectangular pulse waveform by way of the electric circuits according to the present invention. In this way, the pulse generator according to the present invention can be arranged as one electrode pole, and the end of an electrode lead connected to the pulse generator can be arranged as the other electrode pole, outside the patient's thorax (subcutaneous ICD). Due to the possible more compact design, a pulse generator configured as a subcutaneous ICD advantageously has a volume of 70 cm³ or less.

Of course, it is also possible to achieve a lower therapy voltage with the pulse generator according to the present invention, for example 600 V, which allows a use as a conventional ICD, wherein the end of the electrode lead is arranged inside the thorax, and the pulse generator is located outside the thorax. The aforementioned lower therapy voltage can be implemented by smaller energy stores. Due to the possible more compact design, a pulse generator configured as a conventional ICD can accordingly have a volume of 35 cm³ or less.

The pulse generator according to the present invention can also be used in an ICD in which both the end of the electrode lead and the pulse generator are located inside the thorax. In this case, a therapy voltage of approximately 550 V is preferably used, which are implemented with the pulse generator according to the present invention comprising smaller energy stores, so that in particular a device volume of 35 cm² or less can be achieved.

According to one embodiment of the implantable pulse generator according to the present invention, it is provided that the primary energy store and the at least one secondary energy store are connected in series, in particular fixedly or inalterably in series, that is, the aforementioned energy stores are not disconnected by a switch. As a result of this fixed series connection, the electric circuit according to the present invention is advantageously less prone to faults.

According to an alternative embodiment of the implantable pulse generator, it is provided that the primary energy store and the at least one secondary energy store can be connected in series.

According to one embodiment of the implantable pulse generator according to the present invention, it is provided that the activation for the discharge of the at least one secondary energy store takes place in a time-controlled or signal-controlled manner.

The control signal can be derived in the process from an analysis of one or more measuring voltages or currents, which are measured directly at the energy stores or at the delivered pulse, for example in the therapeutic current path.

Accordingly, according to one embodiment of the implantable pulse generator according to the present invention, a device for voltage monitoring is included, which is in particular configured to determine the voltage of each of the energy stores of the implantable pulse generator according to the present invention, preferably continuously or at predefined intervals.

The device for voltage monitoring is preferably further configured to transmit a first signal to the control unit when the voltage of one of the energy stores of the implantable pulse generator according to the present invention drops below a predefined threshold value. The first signal can advantageously trigger the discharge of a further energy store via the therapeutic current path.

The device for voltage monitoring is preferably also configured to transmit a second signal to the control unit when the voltage of one of the energy stores of the implantable pulse generator according to the present invention does not drop below a predefined threshold value within a predefined time. The second signal can advantageously suppress a discharge of a further energy store via the therapeutic current path. In this design, the device for voltage monitoring and the control unit can implement an overvoltage protection system, in particular for the electric circuit according to the present invention. It is established via the voltage measurement whether a load is present on the therapeutic current path (voltage drop) or no load is present (no voltage drop). If no load is detected, no further energy stores are discharged via the therapeutic current path so as not to further increase the voltage, for example in the therapeutic current path.

According to a further embodiment, the implantable pulse generator according to the present invention comprises a device for measuring the impedance of the surrounding tissue (body tissue). The device for the impedance measurement is preferably configured to determine the resistance that causes the discharge (observed by the voltage drop) from a voltage ascertained after the start of the discharge of the primary energy store and/or of the at least one secondary energy store. The voltage can be the therapy voltage, the voltage of an individual energy store, or any voltage within the electric circuit according to the present invention. The voltage can be ascertained in the process by the aforementioned device for voltage monitoring.

According to a further embodiment of the implantable pulse generator according to the present invention, it is provided that the point in time for the start of the second interval of the first phase is determined from the discharge behavior of the first energy store and/or of the at least one secondary energy store. The aforementioned point in time is selected in such a way that the voltage of the particular energy store does not drop below a predefined threshold value, for example 80% of the output voltage.

According to a further embodiment of the implantable pulse generator according to the present invention, it is provided that the electric circuit comprises multiple secondary energy stores, wherein the control unit is configured to activate one or more electric switches of the electric circuit in such a way that the secondary energy stores are sequentially or consecutively discharged via the therapeutic current path in the second interval of the first phase of the pulse delivery.

According to a further embodiment of the implantable pulse generator according to the present invention, it is provided that the primary energy store and the multiple secondary energy stores are connected in series, in particular fixedly or inalterably, that is, in particular without disconnectable switches between the energy stores.

According to an alternative embodiment of the implantable pulse generator, it is provided that the primary energy store and each of the multiple secondary energy stores can be connected in series, wherein in particular the secondary energy stores can be connected in parallel with one another.

In particular, the multiple secondary energy stores can essentially have identical capacitances (that is, within a tolerance of no more than 20%) and/or nominal voltages (that is, within a tolerance of no more than 10%) or different capacitances and/or nominal voltages. In the case of multiple secondary energy stores, these are in each case preferably of the same or an identical type.

According to a further embodiment of the implantable pulse generator according to the present invention, it is provided that in each case one of the secondary energy stores is discharged in the second interval at a respective point in time (either alternately or all consecutively) via the therapeutic current path. Again, the respective point in time is preferably selected in such a way that the voltage of the particular energy store does not drop below a predefined threshold value, for example 80% of the output voltage. Likewise, the respective points in time may be selected in such a way that the therapy voltage does not drop by more than 20% of the maximum voltage or output voltage.

The discharge of the secondary energy store, or energy stores, in the therapeutic current path preferably takes place in such a way that the variation of the actual pulse waveform (peak therapy voltage/current) from the desired ideal rectangular pulse waveform is less than 50%, and preferably less than 20%. Such variations are also referred to as ripple. This is apparent as a spike in the voltage waveform.

The variation (ripple), or variations, can, as described above, be maintained within the aforementioned boundaries by voltage monitoring, wherein the dropping voltage of the exponential partial discharge of the particular energy store is observed. If the voltage drops below a predefined threshold value, the charge of another energy store is called up, wherein the therapy voltage increases to the desired maximum voltage and decreases again with the discharge of the other energy store. This is also apparent by a further spike, or ripple, in the voltage waveform.

The variation (ripple), or variations, can also be controlled in a time-controlled manner as described above. The last secondary energy store whose charge is called up is preferably discharged up to a polarity reversal with a biphasic shock (the last spike in the therapy voltage "decays" until polarity reversal of the shock).

The point in time of the switch to the next energy store can, for example, be ascertained from the exponential law of the energy store discharge, with the time constant being known, having a known capacitance C, and the resistance R determined as described above in such a way that the charge of the activated energy store is equal to the first polarity (+/−20%).

The variation (ripple), or variations, from the ideal pulse waveform can be controlled in such a way that the therapy voltage, each time a switch is made to the next energy store, essentially (+/−20%) increases to the same voltage, that is, the peaks of the ripples are at the same level (+/−20%).

As an alternative, the variation, or the variations, from the ideal pulse waveform can be monitored in such a way that the therapy voltage drops each a switch is made to the next energy store, for example by a maximum of 20% each time.

The aforementioned control of the variation, or variations, can be time-controlled or voltage-controlled as described above.

According to a further embodiment of the implantable pulse generator according to the present invention, it is provided that the control unit is further configured to activate at least one electric switch, preferably multiple switches of a bridge circuit (H-bridge), of the electric circuit in a second phase of the pulse delivery in such a way that the direction of current in the therapeutic current path is reversed. In this way, a steep voltage drop of the pulse can advantageously be achieved at the end of the first phase, and a biphasic therapeutic pulse can be generated. Moreover, areas in the target tissue that were not sufficiently stimulated in the first phase can advantageously be stimulated in the second phase. At the same time, charge equalization can advantageously be achieved in the target tissue, preferably the cardiac tissue.

According to a further embodiment of the implantable pulse generator according to the present invention, it is provided that the control unit is further configured, in a second phase of the pulse delivery:
to activate an electric switch in the electric circuit in such a way that the primary energy store is discharged via the therapeutic current path, or
to activate an electric switch in the electric circuit in such a way that the primary energy store and the secondary energy store, or energy stores, are discharged via the therapeutic current path.

According to an alternative embodiment of the implantable pulse generator according to the present invention, it is provided that the control unit is further configured, at the end of the first phase of the pulse delivery, to activate one or more electric switches in such a way that the primary energy store and/or the secondary energy store, or the multiple secondary energy stores, are disconnected from the therapeutic current path, and/or discharged in one or more bleeder resistors connected thereto. Advantageously, a steep voltage drop of the pulse at the end of the first phase can also be achieved with this embodiment, wherein a monophasic pulse can be generated in the process.

According to a further embodiment of the implantable pulse generator according to the present invention, it is provided that the primary energy store is composed of a plurality of individual energy stores, which are connected in series or in parallel with one another. The number of the individual energy stores is preferably adapted to the required or desired charging capacitance. The primary energy store preferably comprises at least two individual energy stores, three individual energy stores being preferred.

According to a further embodiment of the implantable pulse generator according to the present invention, it is provided that the individual energy stores of the primary energy store are fixedly connected in series.

In particular, the individual energy stores of the primary energy store can essentially have identical capacitances (that is, within a tolerance of no more than 20%) and/or nominal voltages (that is, within a tolerance of no more than 10%) or different capacitances and/or nominal voltages.

According to a further embodiment of the implantable pulse generator according to the present invention, it is provided that the switch, or the switches, of the electric circuit is or are electronic switches or semiconductor switches, in particular selected from: insulated-gate bipolar transistor (IGBT), anode gated thyristor (AGT), or a combination of the aforementioned electronic switches.

According to a further embodiment of the implantable pulse generator according to the present invention, it is provided that at least one of the switches described above is in electrical connection with a diode, wherein the diode is arranged between one of the energy stores and the switch. The diode is preferably configured to block the current in the direction of the energy store. A diode is preferably arranged between each switch and the associated energy store, except for the switch by way of which the last secondary energy store is discharged via the therapeutic current path. Here as well, each of the diodes is preferably configured to block the current in the direction of the particular energy store. In this way, the switches can advantageously be protected against polarity reversal.

According to a further embodiment of the implantable pulse generator according to the present invention, it is provided that the multiple secondary energy stores comprise between two and four secondary energy stores, preferably three secondary energy stores.

According to one embodiment of the implantable pulse generator according to the present invention, it is provided that the energy stores are capacitors or coils. Multiple energy stores, for example multiple secondary energy stores, can be formed by a capacitor in the process, which includes multiple capacitances, which are formed by multiple anodes, for example, wherein the multiple capacitances can be discharged independently of one another.

According to a further embodiment of the implantable pulse generator according to the present invention, it is accordingly provided that the multiple secondary energy stores are formed by a capacitor comprising at least one first electrode having a first polarity, and at least two second electrodes having a second polarity, wherein the first electrode and the at least two second electrodes can be electrically contacted separately from one another from the outside of the capacitor.

According to a further embodiment of the implantable pulse generator according to the present invention, it is provided that the primary energy store and/or the second energy store, or energy stores, are a capacitor comprising at least one cathode and at least two anodes, preferably comprising three anodes, wherein the cathode and the at least two anodes can be electrically contacted separately from one another from the outside of the capacitor. The capacitor preferably comprises an electrically conductive housing, in which the cathode and the anodes are arranged, wherein the housing is in electrical connection with the cathode, and the anodes can be electrically contacted by the housing and one another, via at least one electrical feedthrough from the outside of the capacitor or the capacitor housing. The cathode is preferably formed by an electrolyte, wherein the anodes are preferably formed of a valve metal, preferably aluminum, tantalum or niobium. In particular, each of the anode can form a dedicated capacitance with the cathode (the electrolyte), which is preferably in the range of 200 μF to 300 μF, and in particular approximately 241 μF.

According to a further embodiment of the implantable pulse generator according to the present invention, it is provided that the electric circuit comprises a primary energy store, which comprises three of the capacitors described in the preceding paragraph comprising multi-electrodes, and a secondary energy store, which is formed by a capacitor described in the preceding paragraph, wherein in particular the capacitor configured as the secondary energy store comprises at least two, and preferably three, anodes, which can be electrically contacted independently of one another from the outside of the capacitor, and correspondingly can form at least two, and preferably three, capacitances that can be discharged independently of one another.

According to a further embodiment of the implantable pulse generator according to the present invention, it is provided that the capacitor, or the capacitors, forming the primary energy store, the individual energy stores, or one of the aforementioned secondary energy stores, are electrolytic capacitors or ceramic capacitors or film capacitors, preferably aluminum or tantalum electrolytic capacitors, preferably having an energy density of at least 5 J*cm$^3$.

According to one embodiment of the energy store according to the present invention, it is provided that:
the primary energy store has a capacitance in the range of 150 μF to 300 μF and/or a nominal voltage in the range of 250 V to 300 V, and/or
the secondary energy store has, or the secondary energy stores have, a capacitance in the range of 180 μF to 36 μF and/or a nominal voltage in the range of 250 V to 255 V, independently of one another.

If the primary energy store is formed of multiple individual energy stores, for example two or three, the primary energy store preferably has an overall capacitance in the range of 150 μF to 300 μF.

According to claim 10, a method for delivering an electrical pulse having a substantially rectangular pulse waveform is provided. The method comprises the following steps:
connecting a charged primary energy store to a discharge current path in a first interval of a first phase of a pulse delivery; and
connecting at least one charged secondary energy store to the discharge current path in a second interval of the first phase of the pulse delivery,
wherein the primary energy store and the at least one secondary energy store are fixedly connected, or connectable, in series, and wherein:
in the second interval, the primary energy store and, consecutively, all secondary energy stores are discharged via the therapeutic current path, or
the primary energy store and in each case one of the multiple secondary energy stores are discharged via the therapeutic current path.

The method according to the present invention can advantageously be carried out by way of the implantable pulse generator according to the present invention according to claim 1 or one of the embodiments described above.

According to one embodiment of the method according to the present invention, it is provided that the charged primary energy store and the at least one charged secondary energy store are fixedly connected in series, that is, in particular not disconnected by switches.

According to an alternative embodiment of the method according to the present invention, it is provided that the charged primary energy store and the at least one charged secondary energy store can be connected in series.

According to one embodiment of the method according to the present invention, it is provided that the connection of the at least one secondary energy store to the discharge current path is signal-controlled or time-controlled.

According to one embodiment of the method according to the present invention, it is provided that, in the second interval of the first phase of the pulse delivery, multiple charged secondary energy stores are sequentially or consecutively connected to the discharge current path.

According to one embodiment of the method according to the present invention, it is provided that the charged primary energy store and the multiple charged secondary energy stores are fixedly connected in series, that is, in particular not disconnected by switches.

According to an alternative embodiment of the method according to the present invention, it is provided that the charged primary energy store and the multiple charged secondary energy stores can be connected in series.

According to one embodiment of the method according to the present invention, it is provided that only one charged secondary energy store at a time is connected to the discharge current path, wherein in particular the multiple charged secondary energy stores are in each case consecutively connected to the discharge current path. This can, in particular, be achieved by an electric circuit in which the secondary energy stores can be connected in parallel with one another. In this way, only one secondary energy store at a time and the primary energy store are connected to the discharge current path.

According to one embodiment of the method according to the present invention, it is provided that the multiple charged secondary energy stores are sequentially connected to the discharge current path, wherein in particular all secondary energy stores are consecutively connected to the discharge current path. This can, in particular, be achieved by an electric circuit in which the primary energy store and the secondary energy stores are connected in series with one another. In this way, the primary energy store, a first secondary energy store, and every further secondary energy store are consecutively connected in series with the discharge current path.

According to a further embodiment of the method according to the present invention, it is provided that the connection of the primary energy store and of the at least one secondary energy store, or of the multiple secondary energy stores, is carried out in each case by way of a switch, in particular by way of an electronic switch.

According to a further embodiment of the method according to the present invention, it is provided that the direction of current in the current path is reversed in a second phase of the pulse delivery. Such a reversal in the direction of current can advantageously be implemented by way of a bridge circuit.

According to a further embodiment of the method according to the present invention, it is provided that, in the second phase of the pulse delivery,
only the primary energy store is connected to the discharge current path, or
the primary energy store and the secondary energy store, or energy stores, are connected to the discharge current path.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further features and advantages of the present invention are described hereafter based on the description of the figures of exemplary embodiments. In the drawings.

DETAILED DESCRIPTION

Figure 1:
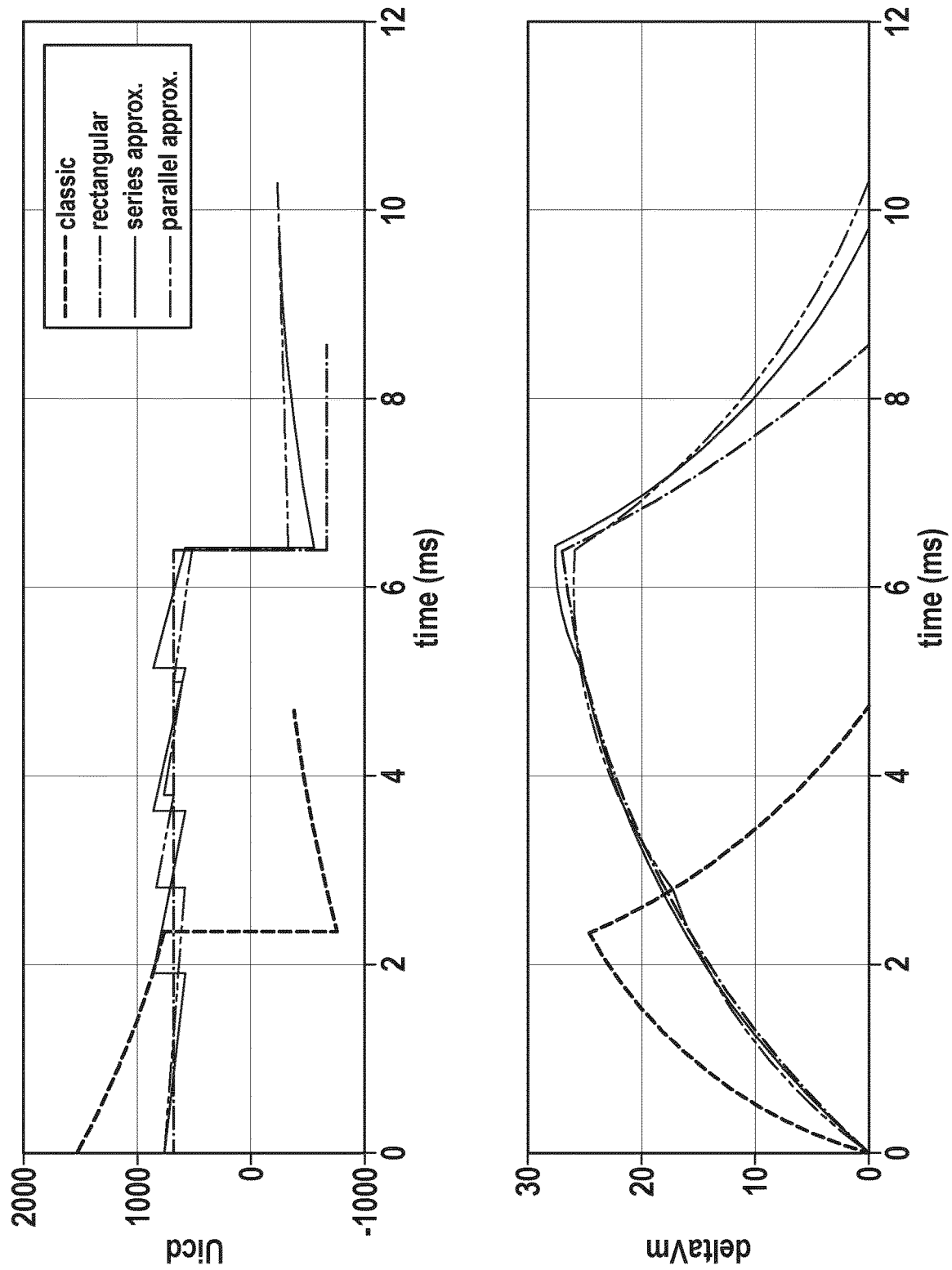
FIG. 1 shows various shock waveforms of implantable defibrillators and the effect on the transmembrane voltage of cardiac muscle cells.

FIG. 1 shows the state of the art (top graph, classic) of the shock waveform of an implantable defibrillator (applicable both to transvenous and subcutaneous ICDs). The therapy voltage results from the discharge of effectively only one capacitor and therefore drops exponentially. This has the disadvantage that the process has to begin with considerably higher starting voltages so as to generate the same effect in the heart. For comparison, the ideal waveform of a shock having a rectangular first phase is shown (rectangular), as well as the shock waveforms of the approach according to the present invention, which approximate the rectangular waveform.

Figure 2A:
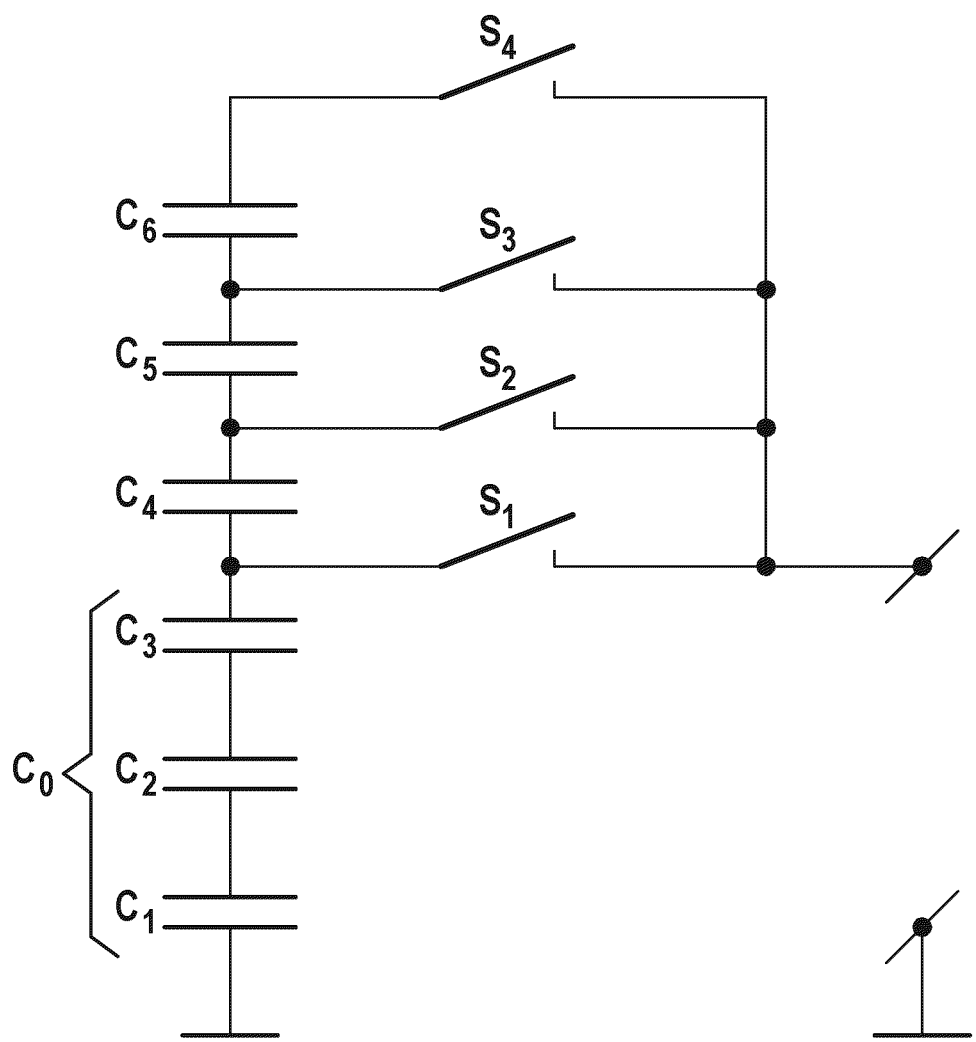
FIG. 2A shows an embodiment of a circuit according to the present invention comprising primary and secondary energy stores that can be connected in series.
Figure 2B:
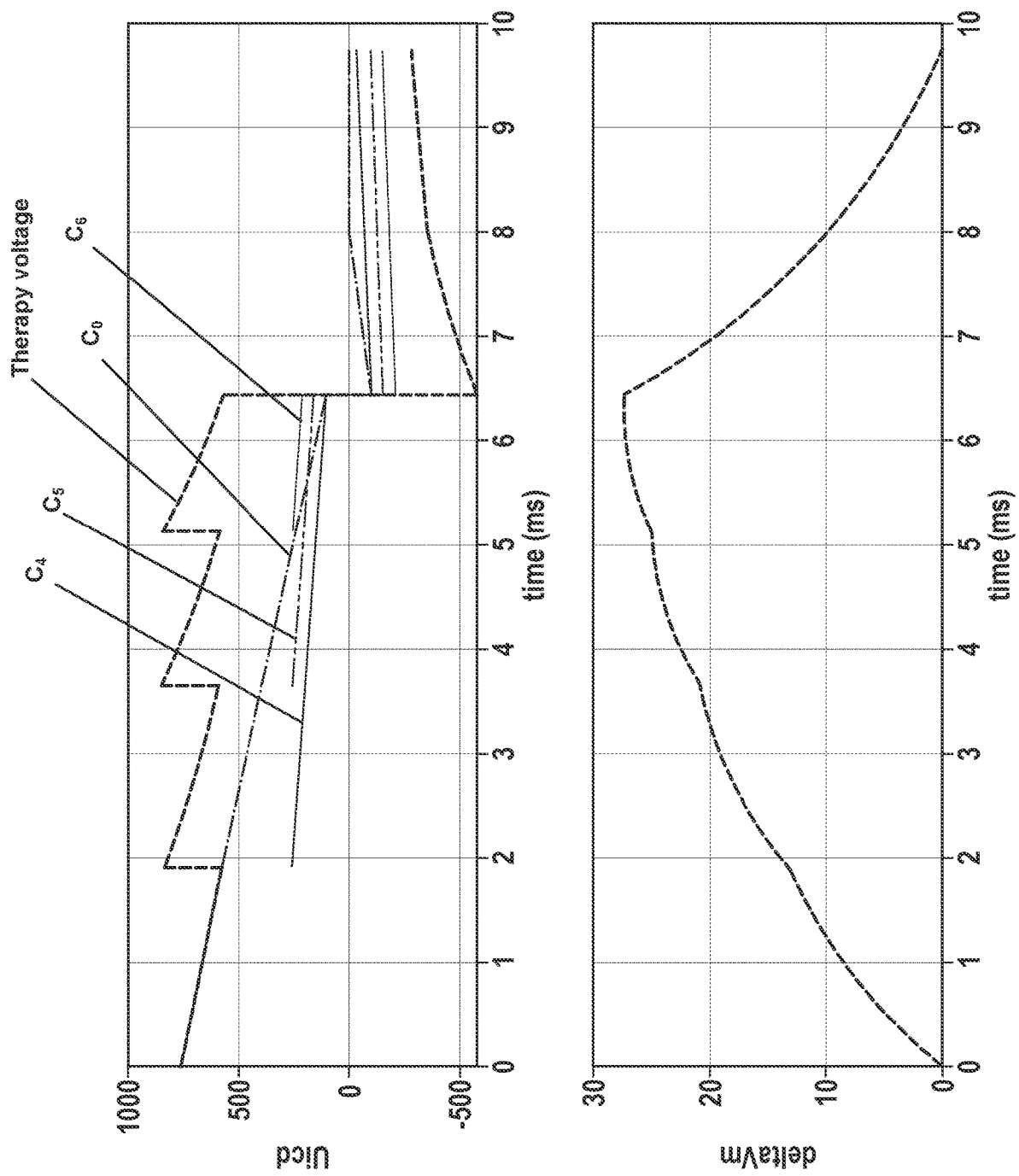
FIG. 2B shows the associated voltage waveform of the therapy voltage and of the energy stores (top), and the effect thereof on the transmembrane voltage of the cardiac muscle cells (bottom)

FIG. 2A shows a preferred embodiment of the circuit according to the present invention, in which the energy stores $C_1$ to $C_6$ are capacitors that are connected, or can be connected, in series. The capacitors $C_1$ to $C_3$, which form the primary energy store according to the present invention, can also be implemented as a capacitance $C_0$. All capacitors $C_1$ to $C_6$ can essentially be charged simultaneously by a charging circuit. The switches $S_1$ to $S_4$ are switched consecutively in ascending order for delivering the therapy. Switch i is opened again in the process before switch i+1 is closed. This circuit further feeds the H-bridge for the generation of the second phase (not shown). One of the switches, preferably $S_4$, is closed in the second phase. Instead of switch S4, it is also possible for a diode to be arranged, which blocks the current in the direction $C_0/C_4$. FIG. 2B shows the voltage waveform of the therapy voltage achievable with this electric circuit, as well as at the capacitors $C_0$, $C_4$, $C_5$, $C_6$ in the top illustration, and the corresponding effect on the transmembrane voltage of the cardiac muscle cells in the bottom illustration. The primary energy store $C_0$, which is formed of three individual energy stores $C_1$ to $C_3$, preferably has an overall capacitance in the range of 150 µF to 300 µF, and each of the secondary energy stores $C_4$ to $C_6$ preferably has a capacitance in the range of 180 µF to 360 µF.

Figure 2C:
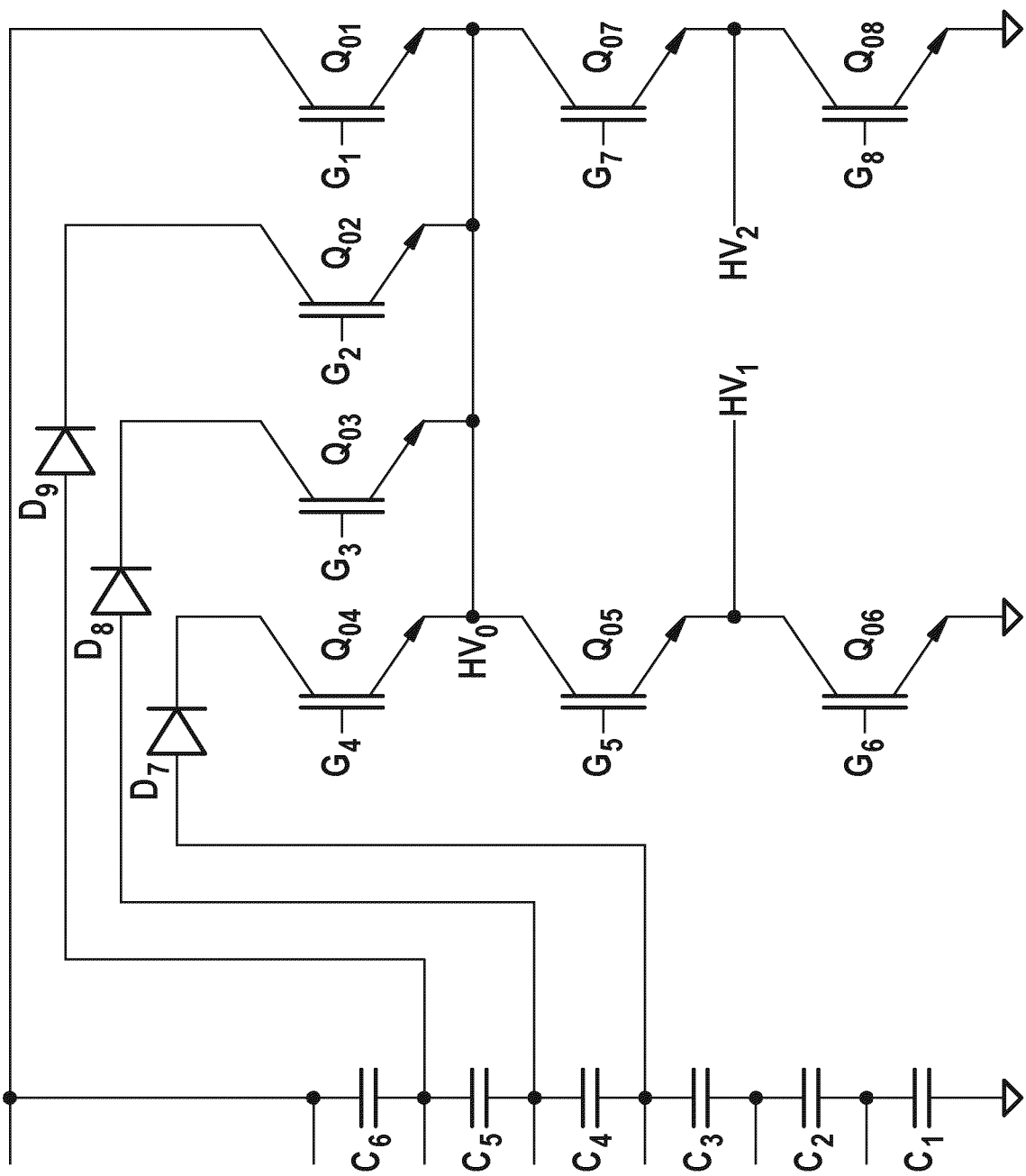
FIG. 2C shows a detailed representation of the embodiment shown in FIG. 2A.

FIG. 2C shows an implementation of the embodiment shown in FIG. 2A comprising electronic switches and up to 6 capacitors as energy stores $C_1$ to $C_6$ of the pulse generator according to the present invention. Of these, 3 capacitors $C_1$, $C_2$, $C_3$ ensure the sufficiently high starting voltage, and the remaining 3 capacitors $C_4$, $C_5$, $C_6$ generate the desired approximately rectangular pulse waveform (saw tooth curve), which in the present case can have up to 4 spikes. So as to render the shock biphasic, an H-circuit comprising the electronic switches (IGBTs) Q05 to Q08 is conventionally used. This circuit is fed via the electronic switches (IGBTs) Q01 to Q04, which activate the capacitors $C_4$, $C_5$, $C_6$. The IGBTs Q02 to Q04 are preferably protected against polarity reversal by way of the diodes D7 to D9. The shock is conducted into the body via the terminals HV1 to HV2. The capacitors are charged via a high voltage source, which is connected to HVin and ground.

Figure 3A:
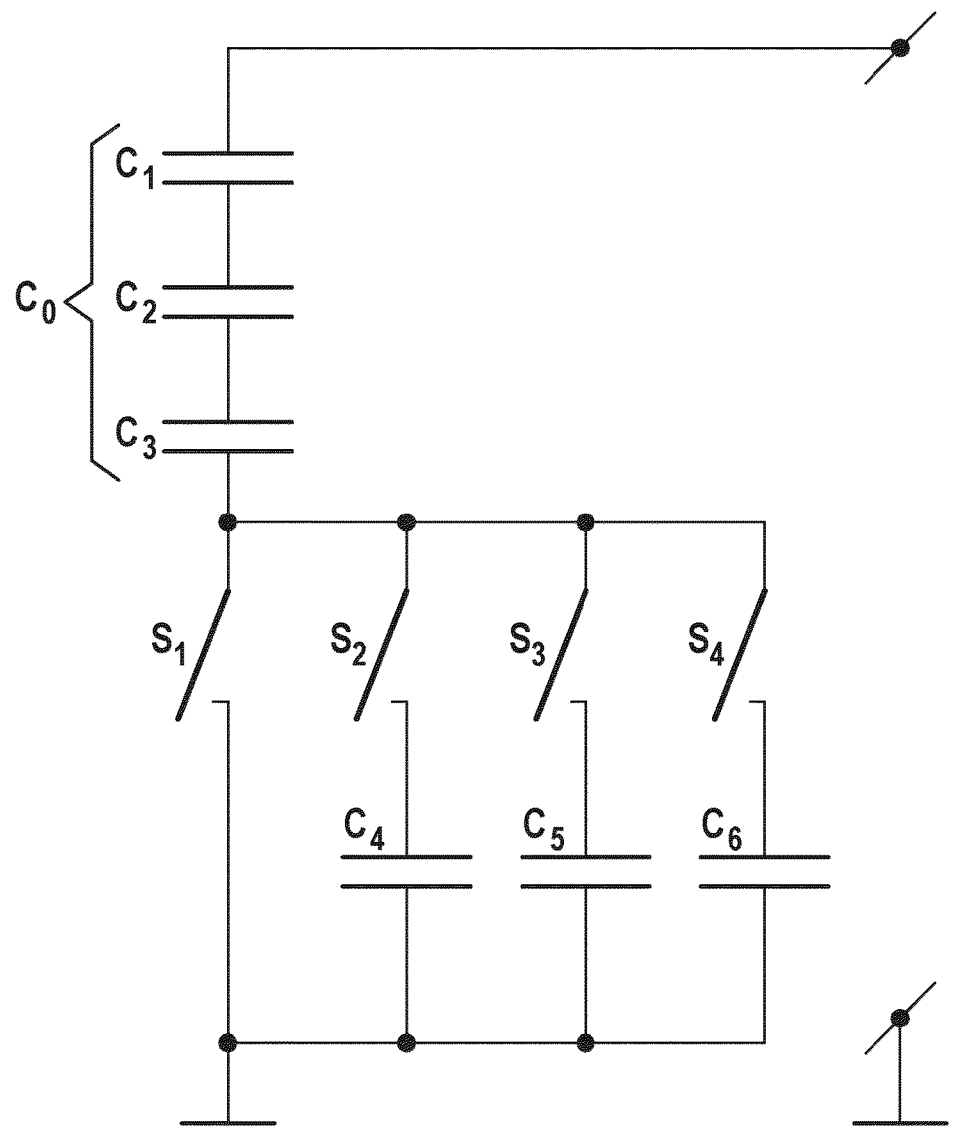
FIG. 3A shows an alternative embodiment of a circuit according to the present invention comprising primary energy stores connectable in series and secondary energy stores connectable in parallel.
Figure 3B:
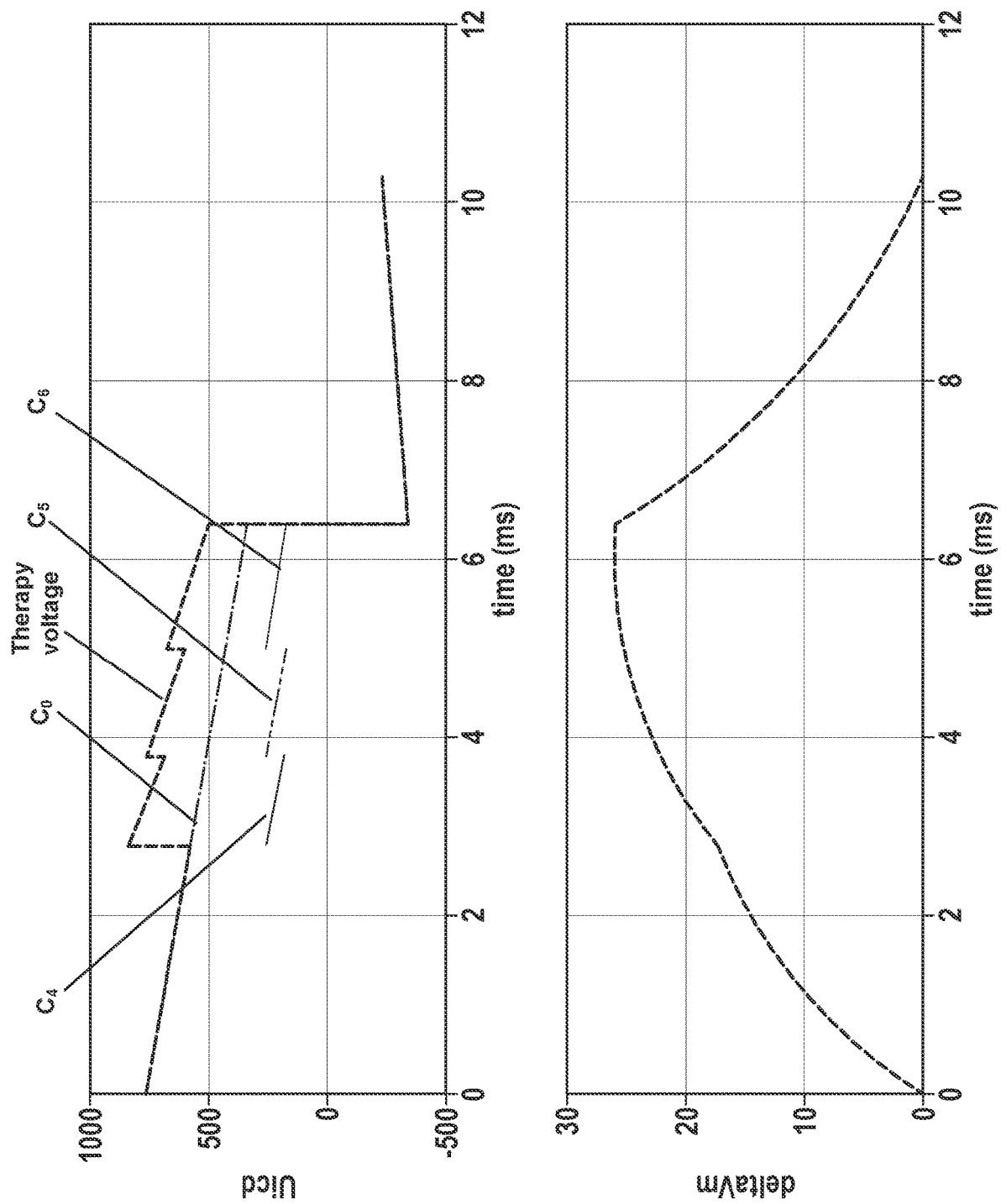
FIG. 3B shows the associated voltage waveform of the therapy voltage and of the energy stores (top), and the effect thereof on the transmembrane voltage of the cardiac muscle cells (bottom)

FIG. 3A shows a further preferred embodiment of the electric circuit according to the present invention comprising capacitors $C_1$ to $C_6$ as energy stores, wherein the activated, or activatable, energy stores $C_4$ to $C_6$ are connected, or connectable, in parallel with one another. The capacitors $C_1$ to $C_3$ can also be implemented as a capacitance $C_0$ here. All capacitors are essentially charged simultaneously by a charging circuit. The switches $S_1$ to $S_4$ are switched consecutively in ascending order for delivering the therapy. Switch i is opened again in the process before switch i+1 is closed. This circuit further feeds the H-bridge for the generation of the second phase. One of the switches, preferably $S_1$, is closed in the second phase. FIG. 3B shows the voltage waveform of the therapy voltage achievable with the electric circuit, as well as at the capacitors $C_0$, $C_4$, $C_5$, $C_6$ in the top illustration, and the corresponding effect on the transmembrane voltage of the cardiac muscle cells in the bottom illustration.

Figure 4:
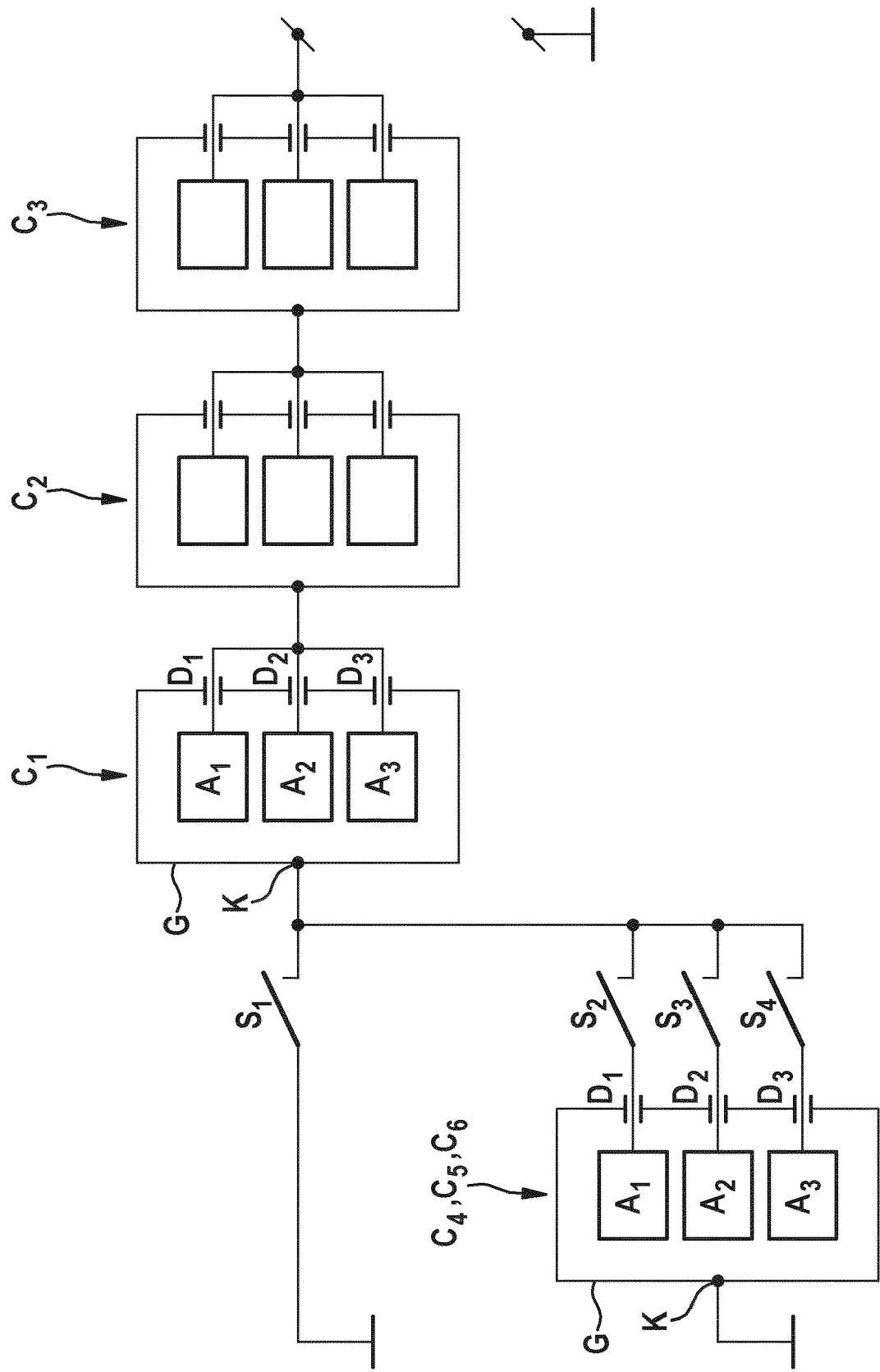
FIG. 4 shows an alternative embodiment of a circuit according to the present invention, using capacitors comprising multi-anodes contactable from the outside.

FIG. 4 shows a preferred embodiment of the electric circuit according to the present invention comprising a parallel approach, using capacitors comprising multi-anodes K, $A_1$, $A_2$, $A_3$ as the primary energy stores $C_0$, $C_1$, $C_2$, $C_3$ and multiple secondary energy stores $C_4$ to $C_6$. In particular, capacitors are used in the process which each comprise a cathode K and, for example, three anodes $A_1$, $A_2$, $A_3$, wherein the cathode K can advantageously be contacted from the outside by an electrically conductive housing, and the anodes can be contacted from the outside separately from one another, and electrically insulated from one another and from the housing G, for example via feedthroughs $D_1$, $D_2$, $D_3$. The multiple secondary energy stores according to the present invention are thus implemented as a capacitor, which provides three capacitances that can be discharged separately from one another with the three separately contactable anodes $A_1$, $A_2$, $A_3$ thereof.

However, it would also be conceivable that the capacitors $C_1$ to $C_3$, which form the primary energy store according to the present invention, are designed in such a way that the anodes $A_1$, $A_2$, $A_3$ are electrically connected in the interior of the housing G, and can be electrically contacted from the outside via a shared anode wire, which is routed to the outside via a feedthrough, for example.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable pulse generator comprising an electric circuit, the electric circuit comprising:
  a primary energy store;
  at least one secondary energy store; and
  a control unit, the control unit being configured to activate one or more electric switches in the electric circuit in such a way that:
    in a first interval of a first phase of a pulse delivery, the primary energy store is discharged via a therapeutic current path, wherein the at least one second energy store is not discharged in the first interval, and
    in a second interval of the first phase of the pulse delivery, the primary energy store and the at least one secondary energy store are discharged via the therapeutic current path,
  the primary energy store and the at least one secondary energy store being inalterably connected in series,
  wherein:
  the implantable pulse generator is designed to deliver a shock having an approximately rectangular pulse waveform.

2. The implantable pulse generator according to claim 1, wherein the electric circuit comprises a plurality of secondary energy stores, the primary energy store and the plurality of energy stores being inalterably connected in series, and the control unit being configured to activate the one or more electric switches of the electric circuit in such a way that the second energy stores of the plurality of secondary energy stores are sequentially or consecutively discharged via the therapeutic current path in the second interval of the first phase of the pulse delivery.

3. The implantable pulse generator according to claim 2, wherein the plurality of secondary energy stores is formed by a capacitor comprising at least one electrode having a first polarity and at least two second electrodes having a second polarity, each electrode being electrically contactable separately from one another from an outside of the capacitor.

4. The implantable pulse generator according to claim 1, wherein the control unit is further configured to activate at least one electric switch of a bridge circuit, in a second phase of the pulse delivery in such a way that the direction of current in the therapeutic current path is reversed.

5. The implantable pulse generator according to claim 1, wherein the primary energy store is composed of a plurality of individual energy stores that are inalterably connected in series or connectable in parallel with one another.

6. The implantable pulse generator according to claim 1, wherein the one or more electrical switches of the electric circuit is an insulated-gate bipolar transistor (IGBT) and/or an anode gated thyristor (AGT).

7. The implantable pulse generator according to claim 1, wherein the electric circuit comprises between two and four secondary energy stores.

8. The implantable pulse generator according to claim 1, wherein the primary energy store and/or the at least one secondary energy store is a capacitor or a coil.

9. The implantable pulse generator according to claim 1, wherein:
  the primary energy store has a capacitance in the range of 150 µF to 300 µF and/or a nominal voltage in the range of 250 V to 255 V, and/or
  the at least one secondary energy store has a capacitance in the range of 180 µF to 360 µF and/or a nominal voltage in the range of 250 V to 255 V.

10. A method for delivering an electrical pulse having a substantially rectangular voltage pulse waveform, the method comprising the following steps:
  connecting a charged primary energy store to a discharge current path in a first interval of a first phase of a pulse delivery; and
  connecting a at least one secondary energy store to the discharge current path in a second interval of the first phase of the pulse delivery,
  the primary energy store and the at least one secondary energy store being inalterably connected in series,
  in the first interval, the at least one second energy store is not discharged, and
  in the second interval, the primary energy store and the at least one secondary energy store being discharged via the therapeutic current path.

11. The method according to claim 10, wherein the at least one secondary energy store comprises a plurality of secondary energy connected to the discharge current path in the second interval of the first phase of the pulse delivery.

12. The method according to claim 11, wherein:
  only one secondary energy store at a time is connected to the discharge current path, or
  the plurality of secondary energy stores is sequentially connected to the discharge current path.

13. The method according to claim 10, wherein the connection of the primary energy store and of the at least one secondary energy store is carried out by way of an electronic switch.

14. The method according to claim 10, wherein a direction of current in the therapeutic current path is reversed in a second phase of the pulse delivery.

* * * * *